United States Patent [19]
Kovar et al.

[11] 4,005,144
[45] Jan. 25, 1977

[54] ETHYNYL-SUBSTITUTED AROMATIC ORTHO DIAMINES AND METHOD OF SYNTHESIS

[75] Inventors: Robert F. Kovar, Dayton; Fred E. Arnold, Centerville, both of Ohio

[73] Assignee: The United States of America as represented by the Secretary of the Air Force, Washington, D.C.

[22] Filed: Apr. 9, 1976

[21] Appl. No.: 675,677

Related U.S. Application Data

[62] Division of Ser. No. 578,847, May 19, 1975, Pat. No. 3,975,444.

[52] U.S. Cl. .......................... 260/578; 260/250 Q; 260/571
[51] Int. Cl.² ................ C07C 87/50; C07C 93/06
[58] Field of Search ............................. 260/578

[56] References Cited

UNITED STATES PATENTS 3,928,450  12/1975  Bilow et al. ................ 260/578 X

OTHER PUBLICATIONS

Allen et al., "Canadian Journal of Chemistry," vol. 41, pp. 1084–1087 (1963).

*Primary Examiner*—Daniel E. Wyman
*Assistant Examiner*—John J. Doll
*Attorney, Agent, or Firm*—Joseph E. Rusz; Cedric H. Kuhn

[57] ABSTRACT

As new compositions of matter, ethynyl-substituted aromatic ortho-diamines. The compounds are useful as endcapping agents for thermally stable heterocyclic oligomeric compositions.

3 Claims, No Drawings

ETHYNYL-SUBSTITUTED AROMATIC ORTHO DIAMINES AND METHOD OF SYNTHESIS

RIGHTS OF THE GOVERNMENT

The invention described herein may be manufactured and used by or for the Government of the United States for all governmental purposes without the payment of any royalty.

This application is a division of our copending U.S. Pat. application Ser. No. 578,847, filed on May 19, 1975, now U.S. Pat. No. 3,975,444.

FIELD OF THE INVENTION

This invention relates to ethynyl-substituted aromatic orthodiamines. In one aspect it relates to a method for synthesizing the compounds.

BACKGROUND OF THE INVENTION

Materials requirements for light-weight, high-temperature composites and adhesives for aircraft and aerospace structural applications have led to the exploration of a number of polymeric systems which might be utilized. One of the most promising classes of candidate materials has been the aromatic heterocyclic polymers. Unfortunately, the most thermally stable systems in this class of materials are formed by condensation reactions with the evolution of volatile by-products. In the fabrication of reinforced composite structures, the volatile by-products, which are evolved, form voids which greatly weaken the structures. Accordingly, there is a real need for a heterocyclic oligomeric material which possesses all the required fabrication criteria and can be converted to a thermally stable, high molecular weight polymer by a non-volatile addition reaction.

It is an object of this invention, therefore, to provide ethynyl-substituted aromatic ortho-diamine compositions which can be used as endcapping agents for heterocyclic oligomers, thereby enabling such systems to cure by addition reactions.

Another object of the invention is to provide methods for preparing intermediates that are used in the synthesis of the endcapping agents.

A further object of the invention is to provide a method for synthesizing the endcapping agents.

Other objects and advantages of the invention will become apparent to those skilled in the art upon consideration of the accompanying disclosure.

SUMMARY OF THE INVENTION

The present invention resides in ethynyl-substituted aromatic ortho-diamines having the following formulas:

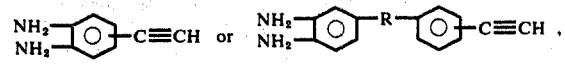

wherein R is oxygen or sulfur and the ethynyl group is ortho, meta or para to R.

The compounds of this invention are useful as endcapping agents for thermally stable heterocyclic oligomeric compositions. The heterocyclic oligomers are those formed from aromatic tetraamines and bis-benzils, bis-glyoxals, dianhydrides, diacids, and the like. When used as endcapping agents, a thermally stable heterocyclic polymer with ethynyl ends groups is provided that cures by non-volatile addition reactions.

The endcapping agents can be reacted with quinoxaline oligomers having glyoxal end groups, benzimidazole oligomers having acid end groups, pyrone oligomers having anhydride end groups, and benzimidazobenzophenanthraline oligomers having anhydride end groups. In particular, the endcapping agents are useful in preparing addition cured phenylquinoxaline compositions by reacting them with phenylquinoxaline oligomers with benzil end groups as disclosed in our copending Pat. application Ser. No. 578,846, filed on May 19, 1975, now U.S. Pat. No. 3,966,729. The disclosure of this copending application is incorporated herein by reference.

One embodiment of the present invention is concerned with the process for preparing the endcapping agents. In accordance with this process, intermediate aromatic dinitro ethynyl compounds are converted to the ethynyl-substituted aromatic ortho-diamines. This conversion is accomplished by reduction of the intermediates with zinc in ammonium hydroxide or with sodium hydrosulfite in aqueous methanol. The reactions involved can be illustrated by the following equations:

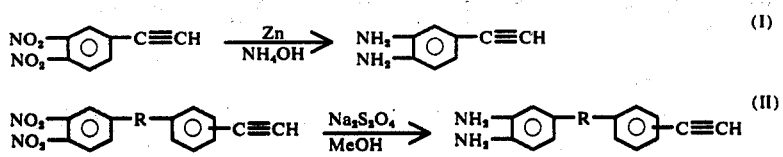

In equation II, R is indicated hereinabove.

The aromatic dinitro ethynyl intermediates employed in the above-described process are also new compositions of matter, and they can be prepared by several different procedures which constitute other embodiments of the invention. In one process dinitro aryl acetyl ether and thio compounds are initially prepared. Thus, these compounds are synthesized by the aromatic nucleophilic substitution of various hydroxy and mercapto acetphenones with 4-fluoro-1,2-dinitrobenzene. The reaction involved is illustrated by the following equation:

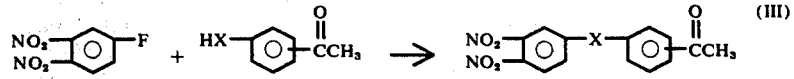

In above equation X is oxygen or sulfur and the acetyl group is ortho, meta or para to X.

The dinitro aryl acetyl compounds of Equation III are converted to the intermediate aromatic dinitro etynyl compounds. This conversion is accomplished by the reaction of the dinitro acetyl compounds with oxalyl chloride or phosphorus oxychloride in N,N'-dimethylformamide (DMF) followed by hydrolysis with an inorganic base. The reactions involved are illustrated by the following equations:

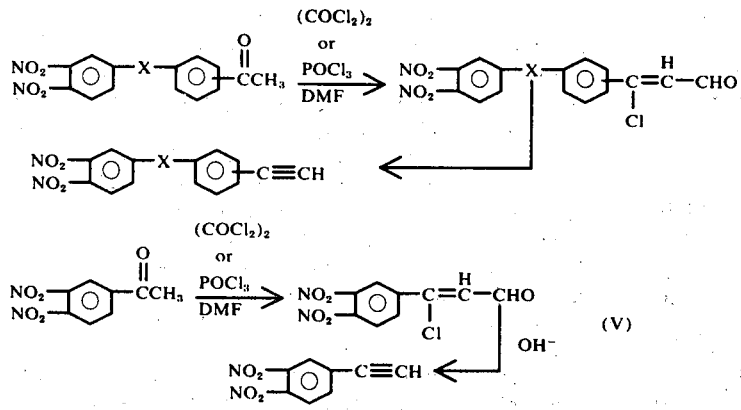

In equation IV, X is as defined hereinabove with the acetyl, chlorocianamaldehyde and ethynyl groups being ortho, meta or para to X. Thus, in the product of equation IV, X is the same as R as defined hereinabove.

The dinitro ethynyl arylether and arylthioether intermediates may also be prepared by aromatic nucleophilic substitution of various hydroxy and mercapto ethynyl benzenes with 4-fluoro-1,2-dinitrobenzene. The hydroxy and mercapto ethynyl benzenes are prepared from tosylated actephenones by going through the formation of the chlorocianamaldehyde group and subsequent hydrolysis reactions. The reactions involved are illustrated by the following equation:

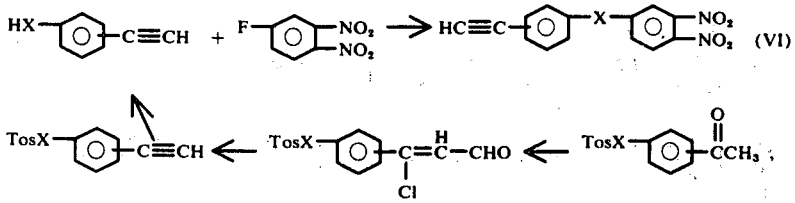

wherein Tos equals

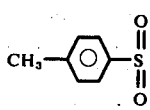

and X is as defined hereinbefore.

A more complete understanding of the invention can be obtained by the following illustrative examples which are not intended, however, to be unduly limitative of the invention.

EXAMPLE I

Preparation of
4-(3-ethynylphenoxy)o-phenylenediamine a. 3'-Acetyl-3,4-dinitrophenyl ether To a solution containing 8.0 g (67 mmoles) of m-hydroxyacetophenone dissolved in 50 ml of dry pyridine was added 2.8 g (approximately 67 mmoles) of solid sodium hydride (57% dispersion in mineral oil). The resulting mixture (frothing) was stirred at room temperature for 3 hours, at which time the flask was cooled to 0°, and 15 g (75 mmoles) of solid 3,4-dinitrofluorobenzene was added all at once. The reaction mixture was allowed to warm to room temperature, and was then heated at 100° C for an additional hour. The contents of the flask were then poured into one liter of water and the resulting mixture extracted with two 100 ml portions of methylene chloride. The combined extracts were washed with two portions of 5% HCl solution and the organic phase evaporated to a volume of 50 ml. The concentrated solution of crude product was filtered through a 2 × 4 inch dry column of silica gel (Voelm) which was eluted with methylene chloride. The eluate was evaporated to dryness, and the residue rechromatographed on a 2 × 12 inch dry column of silica gel. Elution with 1:1 methylene chloride:hexane removed a first band of impurities. Further elution using methylene chloride produced a second band containing the product. Evaporation of the eluate to dryness, and recrystallization of the residue from methylene chloride/absolute ethanol afforded 11.7 g (58%) of yellow crystals, m.p. 140°–141° C. Large crystals of high purity material were obtained by slow spontaneous evaporation of concentrated methylene chloride solutions of 3'-acetyl-3,4-dinitrophenyl ether.

Analysis: Calc'd for $C_{14}H_{10}N_2O_6$: C,55.65; H,3.31; N,9.27. Found: C,55.43; H,3.29; N,9.29.

b. m-(3,4-Dinitrophenoxy)-α-chlorocinnamaldehyde

A 250 ml 1-neck, round-bottomed flask equipped with magnetic stirrer and nitrogen adapter was thoroughly flamed and purged with nitrogen. To the flask was added 25 ml of dry dimethylformamide (DMF) and the flask was cooled to 0° C in an ice bath. Oxalyl chloride (2.5 g – 20 mmoles) was added dropwise to the flask (fuming) under nitrogen over a period of ½ hour, producing a white precipitate of Vilsmeyer complex. After the addition, the reaction mixture was stirred at 0° C for an additional ½ hour, at which time a solution containing 5.0 g (16.5 mmoles) of 3-acetyl-phenyl-3,4-dinitrophenyl ether dissolved in 25 ml of dry DMF was added dropwise, maintaining the bath temperature at 0° C. The cooling was then removed, and the reaction mixture stirred at room temperature for 1 hour, and then at 50° C for an additional hour. The contents of the flask were poured into 500 ml of cold, saturated sodium bicarbonate solution, and the crude product which precipitated was extracted into methylene chloride. The combined extracts were evaporated to a small volume and filtered through a 1 × 4 inch dry column of silica gel, eluting with additional methylene chloride. Evaporation of the elute to dryness yielded m-(3,4-dinitrophenoxy-α-chlorocinnamaldehyde in the form of a yellow powder, m.p., 100°–101° C (40%).

Analysis: Calc'd for $C_{15}H_9N_2O_6Cl$: C,51.07; H,2.60; N,8.03; Cl,10.17. Found: C,51.49; H,2.52; N,7.97; Cl,9.98.

c. 4-(3-Ethynylphenoxy)-o-dinitrobenzene

To 50 ml of refluxing 1N sodium hydroxide solution, under a nitrogen atmosphere, was added a solution containing 10 g (0.028 mole) of m-(3,4-dinitrophenoxy)-α-chlorocinnamaldehyde dissolved in 50 ml of 1,4-dioxane. The dark mixture was refluxed for ½ hour at which time the solution was cooled and acidified with 10% sulfuric acid. The reaction mixture was extracted with several 50 ml portions of ether, and the combined extracts evaporated to dryness. The residue was chromatographed on a 1 × 12 inch dry column of silica gel. Elution of the column using 3/1 hexane/methylene chloride produced a first band of sideproduct. Further elution using 1/1 hexane/methylene chloride yielded a second band which contained the desired product. Evaporation of the eluate to dryness in vacuo afforded 2 g (25%) of 4-(3-ethynylphenoxy)-o-dinitrobenzene as light yellow crystals, m.p. 68°–69° C.

Analysis: Calc'd for $C_{14}H_8O_5$: C,59.16; H,2.84; N,9.86. Found: C,59.01; H,2.82; N,9.85.

d. 4-(3-Ethynylphenoxy)-o-phenylenediamine

To a rapidly stirred suspension of 25 g (0.38 g atom) of powdered zinc in 25 ml of concentrated ammonium hydroxide was added a solution containing 5.0 g (17.6 mmoles) of 4-(3-ethynylphenoxy)-o-dinitrobenzene dissolved in 25 ml of tetrahydrofuran. The mixture was stirred at room temperature for ½ hour, at which time an additional 5 ml of ammonium hydroxide was added, and the solution stirred an additional half hour. At that time, the reaction mixture was filtered by suction, and the residue was washed with several portions of tetrahydrofuran. The filtrate was extracted with several portions of ether, and the combined ether extracts washed with water. Evaporation of the organic layer in vacuo yielded a dark red oil. Chromatography of the residue on 1 × 12 inch dry column of silica gel afforded an initial red band (elution with methylene chloride) of side-product. Further elution using ethyl acetate produced a second band of desired product. Evaporation of solvent in vacuo yielded 3.3 g (84%) of 4-(3-ethynyl-phenoxy)-o-phenylenediamine as a dark orange oil.

Analysis: Calc'd for $C_{14}H_{12}N_2O$: C,74.98; H,5.39; H,12.49. Found: C,74.43; H,5.31; N,11.98.

EXAMPLE II

Preparation of 4-(3-ethynylphenoxy)-o-phenylenediamine from m-hydroxyethynyl benzene a. p-Toluenesulfonate ester of 3-hydroxy-β-chlorocinnamaldehyde A 500 ml 3-necked flask equipped with stirrer, thermometer, condenser and nitrogen inlet adapter was thoroughly flamed and purged with nitrogen. Then, 200 ml of dry N,N-dimethylformamide was added, and the flask was cooled to 20° C. Phosphorus oxychloride (31 g – 0.2 mole) was added dropwise under nitrogen with rapid stirring while maintaining the reaction temperature between 20° and 25° C. After the addition, cooling was discontinued and the solution was stirred for 1 hour. At this point the solution in the flask was dark red in color.

To the opened reaction flask was added rapidly 30 g (0.1 mole) of dry solid 3-acetyl-phenyl-(p-toluene sulfonate). Then solution was stirred at 50° C under nitrogen for 3 hours. The dark yellow mixture was then slowly poured into a four-liter beaker containing 2 liters of stirred, ice-cold sodium bicarbonate solution (20 g $NaHCO_3$). The oily yellow precipitate which gradually separated (2½ hours) was scratched until crystallization occurred. The solid product was then filtered by suction, washed with several portions of water and air-dried. The crude product was dissolved in a minimum amount of methylene chloride (150 ml) and the solution filtered through a 2 × 6 inch dry column of silica gel, eluting with methylene chloride (approximately 500 ml of eluate). Evaporation of the eluate in vacuo yielded 26 g (78%) of the tosylate ester of 3-hydroxy-β-chlorocinnamaldehyde as a pale yellow oil which solidified on cooling, m.p. 67°–68° C.

Analysis: Calc'd for $C_{16}H_{13}SO_4Cl$: C,57.05; H,3.88. Found: C,56.85; H,3.65.

b. 3-Ethynyl-phenyl-p-toluenesulfonate

A solution containing 25 g (74 mmoles) of the p-toluenesulfonate ester of 3-hydroxy-β-chlorocinnamaldehyde dissolved in 100 ml of p-dioxane, previously heated to 80° C, was added to a stirred solution of 5.9 g (148 mmoles) of sodium hydroxide dissolved in 300 ml of water at 80° C. The rapidly stirred mixture was maintained at 80° C for 15 minutes, cooled to room temperature, and then poured into one liter of ice water. The aqueous solution was extracted with three 100 ml portions of ether, and the combined extracts washed with 10% sulfuric acid. Evaporation of the ether yielded a dark oil which was chromatographed on a 2 × 12 inch dry quartz column of silica gel and eluted with 2:1 hexane/methylene chloride solution. Evaporation of the eluate yielded 15 g (76%) of 3-ethynylphenyl-p-toluenesulfonate as a colorless oil which solidified on cooling into white crystals, m.p. 69°–70° C.

Analysis: Calc'd for $C_{15}H_{12}SO_3$: C,66.18, H,4.44. Found: C,66.02; H,4.63.

c. m-Hydroxyethynyl benzene

To a solution containing 4.6 g (83 mmoles) of potassium hydroxide dissolved in 50 ml of methanol was added 7.5 g (27.5 mmoles) of solid 3-ethynylphenyl-p-toluenesulfonate. The mixture was refluxed under nitrogen for 1 hour, at which time the solvent was removed in vacuo at 60° C. The solid residue was extracted into 50 ml of water, and the aqueous solution filtered. The small amount of solid (unreacted starting material) that collected on the filter was rinsed with water, and the filtrate transferred to a separatory funnel and acidified with a 1 N sulfuric acid solution. The slightly acidic solution was extracted with 50 ml portions of methylene chloride, and the combined extracts washed with one 50 ml portion of water. The methylene chloride solution was then reduced in volume to 25 ml, taking care not to exceed 50° C. The concentrated solution of crude product was placed on top of a 1 × 6 inch dry quartz column of silica gel and the column eluted with methylene chloride. The eluate was evaporated to dryness, yielding 3 g (92%) of m-hydroxyethynyl benzene as a colorless oil.

Analysis: Calc'd for $C_8H_6O$: C,81.34; H,5.11. Found: C,81.02; H,4.98.

d. 4-(3-Ethynylphenoxy)-o-dinitrobenzene

To a solution containing 3.0 g (25.4 mmoles) of m-hydroxyethynyl benzene dissolved in 25 ml of dry pyridine was added portionwise 1.1 g (25.4 mmoles) of 57% sodium hydride in mineral oil. The resulting mixture was stirred at room temperature for ½ hour, and then cooled to −20° C. To the cooled solution under nitrogen was added 4.72 g (25.4 mmoles) of solid 3,4-dinitrofluorobenzene. The mixture was stirred at −20° C for 15 minutes, at which time it was allowed to warm to room temperature. Finally, the flask was heated to 100° C for ½ hour and the cooled contents then poured into 200 ml of cold 1N sulfuric acid. The dark oil that separated was extracted into methylene chloride, and the combined extracts washed with water. The methylene chloride solution was reduced in volume to 25 ml, and filtered through a 1 × 4 inch dry column of silica gel, eluting with methylene chloride. Evaporation of the methylene chloride yielded an orange oil. Recrystallization from methanol/water caused solidification to occur. Repeated recrystallization afforded light yellow crystals of 4-(3-ethynylphenoxy)-o-dinitrobenzene, m.p. 68°–69° C.

Analysis Calc'd for $C_{14}H_8N_2O_5$: C,59.16; H,2.84; N,9.86. Found: C,59.31; H,2.82; N,9.65.

e. 4-(3-Ethynylphenoxy)-o-phenylenediamine reduction with sodium hydrosulfite

To a rapidly stirred solution containing 41 g (230 mmoles) of sodium hydrosulfite and 32 g (230 mmoles) of potassium carbonate dissolved in 250 ml of water was added dropwise a solution containing 6.7 g (23.4 mmoles) of 4-(3-ethynylphenoxy)-o-dinitrobenzene dissolved in 50 ml of methanol. The reaction mixture changed from black to white within several minutes after the addition. The white solution was evaporated in vacuo at 50° C to remove the methanol. The remaining aqueous solution was then extracted with several 50 ml portions of methylene chloride. The combined extracts were washed with one 50 ml portion of water, dried over molecular sieves and evaporated to dryness to yield 4.45 g (85%) of 4-(3-ethynylphenoxy)-o-phenylenediamine in the form of a colorless oil.

Analysis Calc'd for $C_{14}H_{12}N_2O$: C,74.98; H,5.39; N,12.49. Found: C,74.63; H,5.21; N,12.22.

EXAMPLE III

Preparation of 3-ethynyl-o-phenylenediamine a. 3,4-Dinitro-α-chlorocinnamaldehyde A 50 ml one-neck, round-bottomed flask equipped with a magnetic stirrer and nitrogen adapter was thoroughly flamed and purged with nitrogen. Then, 25 ml of dry N,N-dimethylformamide was added, and the flask was cooled to 0° C. Freshly distilled oxalyl chloride (6.1 g, 47.6 mmoles) was added dropwise to the flask under nitrogen, producing a white precipitate of Vilsmeyer complex. After the addition, the reaction mixture was stirred at room temperature for 15 minutes, at which time 5.0 g (23.8 mmoles) of solid 3,4-dinitroacetophenone was added. The resulting mixture was stirred at 50° C for ½ hour, at which time the contents of the flask were poured into 200 ml of ice water. The dark oily precipitate was extracted into methylene chloride, and the combined extracts washed with water. The methylene chloride solution was reduced in volume to 25 ml and filtered through a 1 × 4 inch dry column of silica gel, eluting with methylene chloride. Evaporation of the eluate to dryness gave 4.4 g (72% yield) of 3,4-dinitro-α-chlorocinnamaldehyde as a pale yellow oil.

Analysis Calc'd for $C_9H_5N_2O_5Cl$: C,42.13, H,1.96; N,10.92. Found: C,41.99; H,1.82; N,10.46.

b. 3,4-Dinitroethynyl benzene

To 50 ml of a rapidly stirred 0.5 m sodium hydroxide solution maintained at 60° C was rapidly added a solution containing 4.0 g (15.5 mmoles) of 3,4-dinitro-α-chlorocinnamaldehyde dissolved in 10 ml of dioxane. The mixture was stirred for 5 minutes, at which time the solution was cooled and neutralized with 1N sulfuric acid. The reaction mixture was extracted into methylene chloride, and the combined extracts washed with several portions of water. The methylene chloride solution was reduced in volume to 25 ml and filtered through a 1 × 3 inch dry column of silica gel, eluting with methylene chloride. Evaporation of the eluate yielded 1.2 g (40% yield) of 3,4-dinitroethynyl benzene as a light brown oil.

Analysis Calc'd for $C_8H_4N_2O_4$: C,50.01; H,2.10; N,14.58. Found: C,49.98; H,2.06; N,14.44.

c. 4-Ethynyl-o-phenylenediamine

To a rapidly stirred suspension of 4.1 g of powdered zinc in 10 ml of concentrated ammonium hydroxide was added a solution containing 1.2 g (6.3 mmoles) of 3,4-dinitroethynyl benzene dissolved in 10 ml of tetrahydrofuran. The mixture was stirred at room temperature for one-half hour at which time it was filtered by suction and the residue was washed with ether. The filtrate was extracted with ether, and the combined extracts evaporated to dryness. The residual oil was chromatographed on a ½ × 4 inch dry quartz column of silica gel. Elution with methylene chloride removed a first band of impurity, while further elution with ethylacetate produced the product. Evaporation of the eluate to dryness yielded 0.5 g (62% yield) of 4-ethynyl-o-phenylenediamine.

Analysis Calc'd for $C_8H_8N_2$: C,72.70; H,6.10; N,21.20. Found: C,71.83; H,5.90; N,20.22.

EXAMPLE IV

Preparation of endcapped oligomer from 3,3'-diaminobenzidine and 4,4'-(phenylglyoxaloyl)diphenylether.

To a rapidly stirred solution containing 10.2 g (23 mmoles) of 4,4'-(phenylglyoxaloyl)diphenylether and 5 ml of glacial acetic acid in 50 ml of m-cresol was slowly added, under a nitrogen atmosphere, a solution containing 2.5 g (11.7 mmoles) of 3,3'-diaminobenzidine dissolved in 50 ml of m-cresol. After completion of the addition, the reaction mixture was heated at reflux for 1 hour at which time a distilling apparatus was attached to the reaction flask, and m-cresol was distilled until one-half of the original volume remained. To the cooled solution was added 10 ml of glacial acetic acid followed by a solution containing 5.6 g (25 mmoles) of 4-(3-ethynylphenoxy)-o-phenylenediamine dissolved in 20 ml of m-cresol. The mixture was stirred at room temperature for one-half hour and then heated to reflux for 15 minutes during which time m-cresol was distilled from the flask to decrease the volume of the solution to 35 ml. The cooled reaction mixture was then added dropwise to 2 liters of stirred methanol, causing precipitation. The yellow endcapped oligomer has twice reprecipitated from methylene chloride into methanol with the methylene chloride being boiled away each time, yielding 15 g (91% yield) of oligomer.

Analysis Calc'd for $(C_{96}H_{58}N_8O_4)_n$ where $n=1$: C,83.10; H,4.21; N,8.08. Found: C,81.32, H,4.05, N,7.82.

EXAMPLE V

Molded films were fabricated using the endcapped oligomer of Example IV. Neat resin samples were placed between aluminum foil and set in a preheated (various cure temperatures) press and molded at 200 psi. Room temperature tensile strength as a function of time and cure temperatures are listed below in the table.

TABLE

| Cure Temp. °C | Time at Cure Temp., hr | Tensile Strength, psi | Elongation to Break, % |
|---|---|---|---|
| 1. 280 | 5 | 5022 | 2.7 |
| 2. 316 | 1 | 5942 | 2.8 |
| 3. 316 | 5 | 6546 | 2.7 |
| 4. (1) 316 | 1 | | |
| 371 | 1 | 15000 | 2.3 |

(1)Film (4) was postcured for 1 hour at 371° C.

As seen from the foregoing, the present invention provides etnynyl-substituted aromatic ortho-diamines which can be used as endcapping agents for heterocyclic oligomers. The ethynyl terminated oligomers can be readily cured in a short period of time. And because of the curing mechanism, volatile by-products are not evolved, thereby eliminating the presence of voids in the cured products.

As will be evident to those skilled in the art, modifications of the present invention can be made in view of the foregoing disclosure without departing from the spirit and scope of the invention.

We claim:

1. A compound having the following formula:

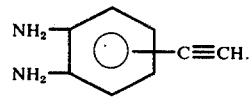

2. The compound according to claim 1 in which the ethynyl group is ortho to the diamine functionality.

3. The compound according to claim 1 in which the ethynyl group is meta to the diamine functionality.

* * * * *